US008868203B2

(12) United States Patent
Armstrong

(10) Patent No.: US 8,868,203 B2
(45) Date of Patent: Oct. 21, 2014

(54) DYNAMIC LEAD CONDITION DETECTION FOR AN IMPLANTABLE MEDICAL DEVICE

(75) Inventor: Randolph K. Armstrong, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 1924 days.

(21) Appl. No.: 11/925,749

(22) Filed: Oct. 26, 2007

(65) Prior Publication Data

US 2009/0112292 A1  Apr. 30, 2009

(51) Int. Cl.
| A61N 1/08 | (2006.01) |
| A61N 1/37 | (2006.01) |
| A61N 1/36 | (2006.01) |
| A61N 1/365 | (2006.01) |
| A61N 1/372 | (2006.01) |

(52) U.S. Cl.
CPC ......... *A61N 1/3706* (2013.01); *A61N 2001/083* (2013.01); *A61N 1/3605* (2013.01); *A61N 1/36542* (2013.01); *A61N 1/37241* (2013.01)
USPC ................................................. 607/63; 607/2

(58) Field of Classification Search
CPC  A61N 1/3605; A61N 1/3706; A61N 1/37241
USPC ...................................................... 607/2, 63
See application file for complete search history.

(56) References Cited

U.S. PATENT DOCUMENTS

| 3,421,511 A | 1/1969 | Schwartz et al. |
| 3,760,812 A | 9/1973 | Timm et al. |
| 3,796,221 A | 3/1974 | Hagfors |
| 4,291,699 A | 9/1981 | Geddes et al. |
| 4,305,402 A | 12/1981 | Katims |
| 4,384,926 A | 5/1983 | Wagner |
| 4,407,303 A | 10/1983 | Akerstrom |
| 4,458,696 A | 7/1984 | Larimore |
| 4,459,989 A | 7/1984 | Borkan |
| 4,573,481 A | 3/1986 | Bullara |

(Continued)

FOREIGN PATENT DOCUMENTS

| WO | 2004/069330    | 8/2004 |
| WO | 2006/116430 A2 | 2/2006 |
| WO | 2006/119131 A1 | 9/2006 |

OTHER PUBLICATIONS

International Search Report dated Feb. 12, 2009; Application No. PCT/US2008/011813; 8 pgs.

(Continued)

*Primary Examiner* — Carl H Layno
*Assistant Examiner* — Jennifer Ghand
(74) *Attorney, Agent, or Firm* — Cyberonics, Inc.

(57) ABSTRACT

A method, apparatus, and system for perform dynamic detection of a lead condition associated with a lead assembly in an implantable medical device that provides a controlled current therapeutic electrical signal to a cranial nerve. A pulsed therapeutic electrical signal is provided to a portion of a patient's body. A multiplicity of feedback signals is provided. Each the signal in the multiplicity comprises a voltage signal associated with the lead assembly for a pulse in the pulsed therapeutic electrical signal. For each the feedback signal, a determination is made as to whether the voltage signal is below a predetermined threshold to create a multiplicity of voltage signal comparison results. A determination is made as to whether or not a lead condition problem exists based upon the multiplicity of voltage signal comparison results.

21 Claims, 9 Drawing Sheets

(56) References Cited

U.S. PATENT DOCUMENTS

| | | |
|---|---|---|
| 4,590,946 A | 5/1986 | Loeb |
| 4,592,359 A | 6/1986 | Galbraith |
| 4,606,349 A | 8/1986 | Livingston et al. |
| 4,608,985 A | 9/1986 | Crish et al. |
| 4,612,934 A | 9/1986 | Borkan |
| 4,628,942 A | 12/1986 | Sweeney et al. |
| 4,630,615 A | 12/1986 | Yomtov |
| 4,649,936 A | 3/1987 | Ungar et al. |
| 4,702,254 A | 10/1987 | Zabara |
| 4,793,353 A | 12/1988 | Borkan |
| 4,821,724 A | 4/1989 | Whigham et al. |
| 4,827,932 A | 5/1989 | Ideker et al. |
| 4,850,356 A | 7/1989 | Heath |
| 4,860,616 A | 8/1989 | Smith |
| 4,867,164 A | 9/1989 | Zabara |
| 4,870,341 A | 9/1989 | Pihl et al. |
| 4,899,750 A | 2/1990 | Ekwall |
| 4,903,700 A | 2/1990 | Whigham et al. |
| 4,920,979 A | 5/1990 | Bullara |
| 4,964,407 A | 10/1990 | Baker, Jr. et al. |
| 4,969,468 A | 11/1990 | Byers et al. |
| 4,979,511 A | 12/1990 | Terry, Jr. |
| 5,003,975 A | 4/1991 | Hafelfinger et al. |
| 5,025,807 A | 6/1991 | Zabara |
| 5,095,905 A | 3/1992 | Klepinski |
| 5,111,815 A | 5/1992 | Mower |
| 5,137,020 A | 8/1992 | Wayne et al. |
| 5,137,021 A | 8/1992 | Wayne et al. |
| 5,139,028 A | 8/1992 | Steinhaus et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,201,808 A | 4/1993 | Steinhaus et al. |
| 5,201,865 A | 4/1993 | Kuehn |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,411,528 A | 5/1995 | Miller et al. |
| 5,431,692 A | 7/1995 | Hansen et al. |
| 5,466,255 A | 11/1995 | Franchi |
| 5,501,702 A | 3/1996 | Plicchi et al. |
| 5,507,786 A | 4/1996 | Morgan et al. |
| 5,522,865 A | 6/1996 | Schulman et al. |
| 5,531,778 A | 7/1996 | Maschino et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,575,813 A | 11/1996 | Edell et al. |
| 5,620,474 A | 4/1997 | Koopman |
| 5,658,318 A | 8/1997 | Stroetmann et al. |
| 5,690,681 A | 11/1997 | Geddes et al. |
| 5,700,282 A | 12/1997 | Zabara |
| 5,707,400 A | 1/1998 | Terry, Jr. et al. |
| 5,713,936 A | 2/1998 | Staub et al. |
| 5,741,311 A | 4/1998 | Mc Venes et al. |
| 5,743,860 A | 4/1998 | Hively et al. |
| 5,755,742 A | 5/1998 | Schuelke et al. |
| 5,755,747 A | 5/1998 | Daly et al. |
| 5,759,199 A | 6/1998 | Snell et al. |
| 5,769,873 A | 6/1998 | Zadeh |
| 5,796,044 A | 8/1998 | Cobian et al. |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,916,239 A | 6/1999 | Geddes et al. |
| 5,919,220 A | 7/1999 | Stieglitz et al. |
| 5,928,272 A | 7/1999 | Adkins et al. |
| 5,995,868 A | 11/1999 | Osorio et al. |
| 6,035,237 A | 3/2000 | Schulman et al. |
| 6,052,624 A | 4/2000 | Mann |
| 6,073,050 A | 6/2000 | Griffith |
| 6,104,956 A | 8/2000 | Naritoku et al. |
| 6,154,678 A | 11/2000 | Lauro |
| 6,171,239 B1 | 1/2001 | Humphrey |
| 6,181,969 B1 | 1/2001 | Gord |
| 6,208,902 B1 | 3/2001 | Boveja |
| 6,212,431 B1 | 4/2001 | Hahn et al. |
| 6,216,045 B1 | 4/2001 | Black et al. |
| 6,259,951 B1 | 7/2001 | Kuzma et al. |
| 6,269,270 B1 | 7/2001 | Boveja |
| 6,304,787 B1 | 10/2001 | Kuzma et al. |
| 6,317,633 B1 | 11/2001 | Jorgenson et al. |
| 6,339,725 B1 | 1/2002 | Naritoku et al. |
| 6,341,236 B1 | 1/2002 | Osorio et al. |
| 6,393,325 B1 | 5/2002 | Mann et al. |
| 6,400,988 B1 | 6/2002 | Gurewitsch |
| 6,418,348 B1 | 7/2002 | Witte |
| 6,445,951 B1 | 9/2002 | Mouchawar |
| 6,453,198 B1 | 9/2002 | Torgerson et al. |
| 6,456,481 B1 | 9/2002 | Stevenson |
| 6,473,653 B1 | 10/2002 | Schallhorn et al. |
| 6,477,417 B1 | 11/2002 | Levine |
| 6,490,486 B1 | 12/2002 | Bradley |
| 6,505,074 B2 | 1/2003 | Boveja et al. |
| 6,510,332 B1 | 1/2003 | Greenstein |
| 6,529,774 B1 | 3/2003 | Greene |
| 6,553,263 B1 | 4/2003 | Meadows et al. |
| 6,556,868 B2 | 4/2003 | Naritoku et al. |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,600,957 B2 | 7/2003 | Gadsby |
| 6,606,523 B1 | 8/2003 | Jenkins |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,648,823 B2 | 11/2003 | Thompson |
| 6,658,294 B1 | 12/2003 | Zadeh et al. |
| 6,662,053 B2 | 12/2003 | Borkan |
| 6,671,556 B2 | 12/2003 | Osorio et al. |
| 6,684,105 B2 | 1/2004 | Cohen et al. |
| 6,687,538 B1 | 2/2004 | Hrdlicka et al. |
| 6,690,974 B2 | 2/2004 | Archer et al. |
| 6,711,440 B2 | 3/2004 | Deal et al. |
| 6,718,203 B2 | 4/2004 | Weiner et al. |
| 6,718,207 B2 | 4/2004 | Connelly |
| 6,721,600 B2 | 4/2004 | Jorgenson et al. |
| 6,721,603 B2 | 4/2004 | Zabara et al. |
| 6,725,092 B2 | 4/2004 | MacDonald et al. |
| 6,731,979 B2 | 5/2004 | MacDonald |
| 6,745,077 B1 | 6/2004 | Griffith et al. |
| 6,754,539 B1 | 6/2004 | Erickson et al. |
| 6,757,566 B2 | 6/2004 | Weiner et al. |
| 6,760,624 B2 | 7/2004 | Anderson et al. |
| 6,760,625 B1 | 7/2004 | Kroll |
| 6,760,628 B2 | 7/2004 | Weiner et al. |
| 6,763,268 B2 | 7/2004 | MacDonald et al. |
| 6,778,856 B2 | 8/2004 | Connelly et al. |
| 6,792,316 B2 | 9/2004 | Sass |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,804,557 B1 | 10/2004 | Kroll |
| 6,819,954 B2 | 11/2004 | Connelly |
| 6,819,958 B2 | 11/2004 | Weiner et al. |
| 6,829,509 B1 | 12/2004 | MacDonald et al. |
| 6,843,870 B1 | 1/2005 | Bluger |

(56) References Cited

U.S. PATENT DOCUMENTS

| | | | |
|---|---|---|---|
| 6,845,266 B2 | 1/2005 | Weiner et al. |
| 6,850,805 B2 | 2/2005 | Connelly et al. |
| 6,875,180 B2 | 4/2005 | Weiner et al. |
| 6,901,290 B2 | 5/2005 | Foster et al. |
| 6,906,256 B1 | 6/2005 | Wang |
| 6,907,295 B2 | 6/2005 | Gross et al. |
| 6,920,357 B2 | 7/2005 | Osorio et al. |
| 6,925,328 B2 | 8/2005 | Foster et al. |
| 6,944,489 B2 | 9/2005 | Zeijlemaker et al. |
| 6,949,929 B2 | 9/2005 | Gray et al. |
| 6,954,674 B2 | 10/2005 | Connelly |
| 6,961,618 B2 | 11/2005 | Osorio et al. |
| 6,985,775 B2 | 1/2006 | Reinke et al. |
| 6,993,387 B2 | 1/2006 | Connelly et al. |
| 7,006,859 B1 | 2/2006 | Osorio et al. |
| 7,010,357 B2 | 3/2006 | Helfer et al. |
| 7,013,174 B2 | 3/2006 | Connelly et al. |
| 7,015,393 B2 | 3/2006 | Weiner et al. |
| 7,047,074 B2 | 5/2006 | Connelly et al. |
| 7,054,686 B2 | 5/2006 | MacDonald |
| 7,107,097 B2 | 9/2006 | Stern et al. |
| 7,123,013 B2 | 10/2006 | Gray |
| 7,171,166 B2 | 1/2007 | Ng et al. |
| 7,174,219 B2 | 2/2007 | Wahlstrand et al. |
| 7,212,869 B2 | 5/2007 | Wahlstrom et al. |
| 7,221,981 B2 | 5/2007 | Gliner |
| 7,239,924 B2 | 7/2007 | Kolberg |
| 7,289,856 B1 | 10/2007 | Karicherla |
| 7,584,004 B2 | 9/2009 | Caparso et al. |
| 2002/0072782 A1 | 6/2002 | Osorio et al. |
| 2003/0083726 A1 | 5/2003 | Zeijlemaker et al. |
| 2003/0176807 A1* | 9/2003 | Goetz et al. ............... 600/547 |
| 2003/0195601 A1 | 10/2003 | Hung et al. |
| 2004/0015205 A1 | 1/2004 | Whitehurst et al. |
| 2004/0147992 A1 | 7/2004 | Bluger et al. |
| 2004/0167583 A1 | 8/2004 | Knudson et al. |
| 2004/0172088 A1 | 9/2004 | Knudson et al. |
| 2004/0210291 A1 | 10/2004 | Erickson |
| 2005/0015128 A1 | 1/2005 | Rezai et al. |
| 2005/0016657 A1 | 1/2005 | Bluger |
| 2005/0107858 A1 | 5/2005 | Bluger |
| 2005/0154426 A1 | 7/2005 | Boveja et al. |
| 2005/0154435 A1 | 7/2005 | Stern et al. |
| 2005/0222642 A1 | 10/2005 | Przybyszewski et al. |
| 2005/0272280 A1 | 12/2005 | Osypka |
| 2006/0058597 A1 | 3/2006 | Machado et al. |
| 2006/0106430 A1 | 5/2006 | Fowler et al. |
| 2006/0167497 A1 | 7/2006 | Armstrong et al. |
| 2006/0173493 A1 | 8/2006 | Armstrong et al. |
| 2006/0184211 A1 | 8/2006 | Gaunt et al. |
| 2006/0224199 A1 | 10/2006 | Zeijlemaker et al. |
| 2006/0253164 A1 | 11/2006 | Zhang et al. |
| 2006/0265024 A1* | 11/2006 | Goetz et al. ............... 607/48 |
| 2006/0265025 A1 | 11/2006 | Goetz et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0060991 A1 | 3/2007 | North et al. |
| 2007/0073150 A1 | 3/2007 | Gopalsami et al. |
| 2007/0100392 A1 | 5/2007 | Maschino et al. |
| 2007/0142889 A1 | 6/2007 | Whitehurst et al. |
| 2007/0173902 A1 | 7/2007 | Maschino et al. |
| 2007/0179557 A1 | 8/2007 | Maschino et al. |
| 2007/0179579 A1 | 8/2007 | Feler et al. |
| 2007/0179584 A1 | 8/2007 | Gliner |
| 2008/0033503 A1 | 2/2008 | Fowler et al. |
| 2008/0046035 A1 | 2/2008 | Fowler et al. |
| 2008/0071323 A1 | 3/2008 | Lowry et al. |
| 2008/0200925 A1 | 8/2008 | Johnson |
| 2008/0215110 A1 | 9/2008 | Gunderson et al. |
| 2008/0255582 A1 | 10/2008 | Harris |
| 2009/0076567 A1 | 3/2009 | Fowler et al. |

OTHER PUBLICATIONS

J. Walter Woodbury and Dixon M. Woodbury, Vagal Stimulation Reduces the Severity of Maximal Electroshock Seizures in Intact Rates: Use of a Cuff Electrode for Stimulating and Recording, Department of Physiology, School of Medicine, University of Utah, Jan. 1991, pp. 94-107, vol. 14, Salt Lake City, Utah.

Mesut Sahin, Improved Nerve Cuff Electrode Recordings with Sub-threshold Anodic Currents, IEEE Transactions on Biomedical Engineering, Aug. 1998, pp. 1044-1050, vol. 45, No. 8.

Peter J. Basser and Bradley J. Roth, New Currents in Electrical Stimulation of Excitable Tissues, Annu. Rev. Biomed. Eng. 2000, vol. 2, pp. 377-397.

* cited by examiner

DYNAMIC LEAD CONDITION DETECTION FOR AN IMPLANTABLE MEDICAL DEVICE

BACKGROUND OF THE INVENTION

1. Field of the Invention

This invention relates generally to implantable medical devices, and more particularly to methods, apparatus, and systems for dynamically monitoring intermittent lead condition problems associated with an implantable medical device.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated by reference in its entirety in this specification. Electrical stimulation of the vagus nerve may be provided by implanting an electrical device underneath the skin of a patient and performing a detection and electrical stimulation process. Alternatively, the system may operate without a detection system if the patient has been diagnosed with epilepsy, and may periodically apply a series of electrical pulses to the vagus (or other cranial) nerve intermittently throughout the day, or over another predetermined time interval.

Typically, implantable medical devices (IMDs) involving the delivery of electrical pulses to body tissues, such as pacemakers (heart tissue) and vagus nerve stimulators or spinal cord stimulators (nerve tissue), comprise a pulse generator for generating the electrical pulses and a lead assembly coupled at its proximal end to the pulse generator terminals and at its distal end to one or more electrodes in contact with the body tissue to be stimulated.

Occasionally, damage to the lead assembly can occur, which may cause various operational problems. Impedance measurements may be used to assess the integrity of the electrical leads that deliver the stimulation provided by a pulse generator. A change in the impedance across the leads that deliver the electrical pulses may be indicative of either or both of changes in a patient's body or changes in the electrical leads themselves. For example, damage in the lead, which may be induced by a break in one or more filaments in a multifilament lead wire, or changes in the body tissue where stimulation is delivered, may affect the efficacy of the stimulation therapy. Therefore, it is desirable for changes in the lead impedance, which may be indicative of various changes or malfunctions, to be accurately detected.

For instance, the integrity of the leads that deliver stimulation is of interest to insure that the proper therapy dosage is delivered to the patient. Some IMDs, most notably pacemakers, provide a voltage-controlled output that is delivered to one or more body locations (typically the heart). Other IMDs, such as a vagus nerve stimulator device developed by Cyberonics, Inc., provide a current-controlled output. Generally, however, state-of-the-art measurements of lead impedance involve an analysis of the delivery of a voltage signal from a capacitive (C) energy storage component through the resistive (R) lead impedance and an examination of the decay of that signal based upon a time-constant proportional to the product of the resistance and capacitance (RC). The total equivalent impedance present at the leads and the known energy source total equivalent capacitance cause a time-constant discharge curve. As the voltage on the capacitance is discharged through the resistance, the exponential decay of this voltage may be monitored to determine the decay time constant RC. From that time constant and an estimate of the known equivalent capacitance C, the equivalent resistance R presented by the leads may be mathematically estimated. However, this type of measurement may lead to inaccuracies for a number of reasons, including the fact that the discharging of the voltage signal may be affected by other resistances and capacitances in the system, the accuracy of the capacitor, the time, voltage, and algorithmic accuracies of the measurement system, and the like.

The quality and integrity of the electrical signals that are sent via the leads are important in proper delivery of therapy. However, leads may occasionally fail, exhibiting problems, such as an electrical short, or a break in one or more conductors associated with the lead. State of the art implantable medical devices offer integrity tests to diagnose lead failures. Direct or indirect lead impedance measurements may be employed, which may identify dramatic or gross lead failures. However, these state of the art analyses may not detect intermittent failures. Intermittent failures can occur for a variety of reasons and may only occur during certain time periods or during certain physical movements by the patient. Normally, leads may be connected properly to a conductor when the lead is in a "positional range" (i.e., proper position where conductors of the lead are properly electrically connected). Outside this positional range, the conductor associated with the lead may lose electrical connection with the lead. This may result in position-dependent intermittent loss of therapy. Further, this type of problem may be difficult to detect. Designers have attempted to alleviate some of these problems by performing periodic impedance measurements. However, the more the frequent the impedance measurements, the more energy that is consumed, and thereby, essential battery life may be prematurely diminished.

The present invention is directed to overcoming, or at least reducing, the effects of, one or more of the problems set forth above.

SUMMARY OF THE INVENTION

In one aspect of the present invention, a method is provided for performing a dynamic detection of a lead condition associated with a lead assembly in an implantable medical device for providing a controlled current therapeutic electrical signal to a cranial nerve. A pulsed therapeutic electrical signal is provided to a portion of a patient's body. A multiplicity of feedback signals is provided. Each the signal in the multiplicity comprises a voltage signal associated with the lead assembly for a pulse in the pulsed therapeutic electrical signal. For each the feedback signal, a determination is made as to whether the voltage signal is below a predetermined threshold to create a multiplicity of voltage signal comparison results. A determination is made as to whether or not a lead condition problem exists based upon the multiplicity of voltage signal comparison results.

In another aspect of the present invention, a method is provided for performing a substantially continuous assessment of a lead condition associated with a lead assembly in an implantable medical device for providing a pulsed therapeutic electrical signal to a cranial nerve. A pulsed therapeutic electrical signal is provided to a portion of a patient's body. A multiplicity of feedback signals is provided. Each the feedback signal is indicative of a condition of a pulse of the pulsed therapeutic electrical signal. At least one of the multiplicity of the feedback signals being asserted in response to a determination that the voltage of a corresponding pulse from the multiplicity of pulses is below a predetermined threshold. A determination is made as to an impedance of the lead assembly is sufficiently out of a predetermined range of tolerance to indicate that a lead condition problem exists during at least one time period of at least one of the multiplicity of pulses, in response to the determination that the voltage of the corresponding pulse from the multiplicity of pulses is below a predetermined threshold.

In another aspect of the present invention, an implantable medical device for performing a dynamic detection of a lead condition associated with a lead assembly coupled to the implantable medical device. The implantable medical device comprises a stimulation unit to provide a pulsed therapeutic electrical stimulation signal to a cranial nerve through a lead operatively coupled to the IMD. The implantable medical device also includes a controller operatively coupled to the stimulation unit. The controller is adapted to determine that a lead condition problem exists in response to at least one determination that at least one of a multiplicity of feedback signals has been asserted. The feedback signals being asserted in response to a determination that a voltage signal corresponding to at least one of a plurality of pulses of the therapeutic electrical signal is outside a predetermined range of tolerance during at least a portion of a time period during which the at least one of the pulses of the therapeutic electrical signal is provided to the cranial nerve,. The controller is also adapted to record a plurality of instances of determinations that the voltage signal associated with the lead assembly is above the predetermined threshold.

BRIEF DESCRIPTION OF THE DRAWINGS

The invention may be understood by reference to the following description taken in conjunction with the accompanying drawings, in which like reference numerals identify like elements, and in which.

Figure 1A:
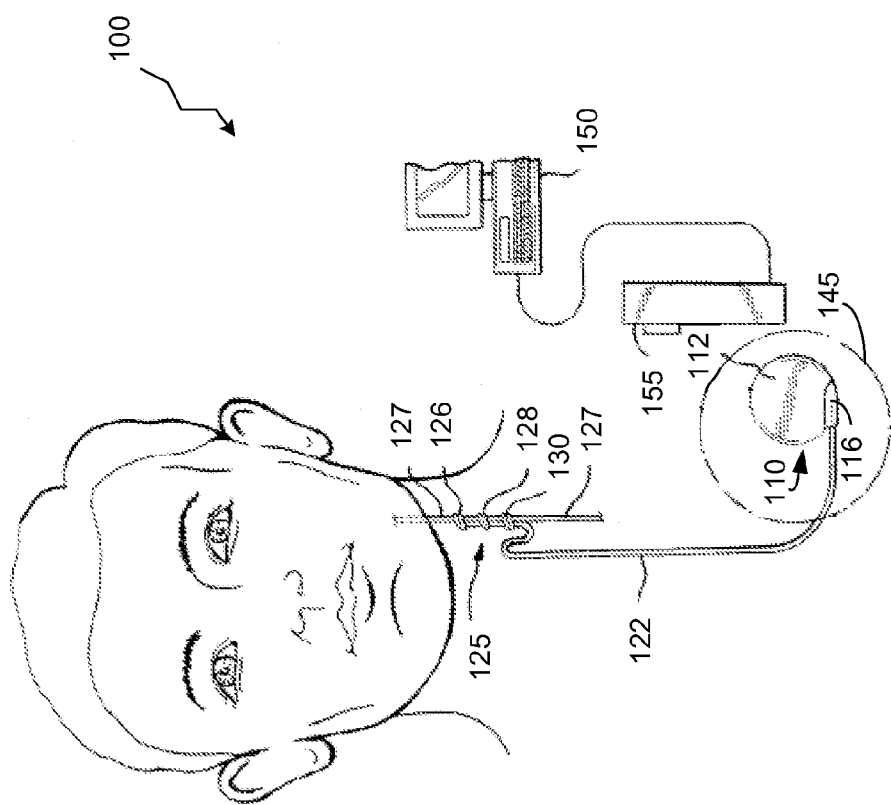
FIGS. 1A-1C are stylized diagrams of an implantable medical device suitable for use in the present invention implanted into a patient's body (FIG. 1A), a detail view of a lead and electrode coupled to a vagus nerve (FIG. 1B), and a front view of an implantable medical device suitable for use in embodiments of the present invention (FIG. 1C)

While the invention is susceptible to various modifications and alternative forms, specific embodiments thereof have been shown, by way of example, in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Cranial nerve stimulation has been proposed to treat a number of medical conditions pertaining to or mediated by one or more structures of the nervous system of the body, including epilepsy and other movement disorders, depression, anxiety disorders, bipolar disorder, autism and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult. Moreover, even if such pathways were known, the precise stimulation parameters that would modulate particular pathways relevant to a particular disorder generally cannot be predicted.

Embodiments of the present invention provide for performing a dynamic lead condition assessment of one or more leads coupled to an implantable medical device (IMD). In one embodiment, the apparatus, system and method provided herein are capable of performing a substantially continuous lead condition detection during delivery of a controlled current therapeutic electrical signal. Embodiments of the present invention provide for utilizing a feedback signal associated with a therapeutic electrical signal to perform an assessment of the impedance associated with a lead assembly. Utilizing principles of Ohm's Law, the feedback signal may be analyzed to determine whether a desired voltage was indeed present during the delivery of the controlled current stimulation signal. Based upon this determination, an assessment of the lead impedance may be performed. This would provide an indication whether the impedance was higher or lower than expected, based upon the controlled current therapeutic electrical signal, and the resultant voltage that the IMD provided to maintain the controlled current signal. In other words, based upon the expected maximum lead impedance, a determination whether the actual impedance is within an acceptable range from the expected impedance may be determined based on the delivered current and the feedback voltage. Based upon this determination, an assessment may be made that the impedance of the lead is higher or lower than the expected value. This may indicate that, during a particular portion of a controlled current therapeutic electrical signal delivered to the nerve, the lead may have malfunctioned. That is, during actual delivery of a therapeutic electrical signal, a process for detecting an intermittent lead condition problem may be performed. The term "lead condition problem" may include a lead break and/or an electrical short associated with conductors coupled to the lead.

A feedback signal corresponding to a particular portion of the delivered therapeutic electrical signal may be used to determine whether the actual lead impedance at a given moment of time is within a predetermined acceptable range from the maximum expected lead impedance. In some embodiments, feedback signals corresponding to substantially all pulses delivered as therapeutic electrical signals may be used to perform a substantially continuous assessment of the lead impedance. Accordingly, a substantially continuous examination of the lead condition may be performed, providing for the detection of substantially all intermittent lead problems, many of which would not otherwise have been detected.

Still further, when an out-of-tolerance lead impedance is detected, this particular occurrence may be stored for later analysis, including a timestamp and the actual value of the lead impedance. Also, when an out-of-tolerance lead impedance is detected, various correlations to the out-of-tolerance lead impedance occurrence may be performed. For example, the out-of-tolerance lead impedance occurrence may be correlated to a particular activity performed by the patient, a physiological parameter, a particular time period, etc. This analysis may provide an indication as to what type of activity performed by the patient, or what type of physiological parameter in the patient's body, causes or contributes to a lead malfunction. In this manner, the cause of the lead condition problem may be isolated.

Further, a healthcare professional may use additional analysis, such as x-rays, etc., when a particular lead error is detected. For example, a healthcare professional may use an external device, e.g., a hand-held device, such as a programmable wand, to continuously assess a lead problem as a patient is placed through several physical positions, to isolate a particular position that may cause an intermittent lead condition problem, e.g., a lead break. When this position is isolated, additional analysis, such as x-rays, etc., may be performed in order to more efficiently correct the lead problems. Utilizing embodiments of the present invention, intermittent lead failures that otherwise may previously have been missed may now be detected, and the cause of such intermittent failures may also be determined.

Figure 1C:
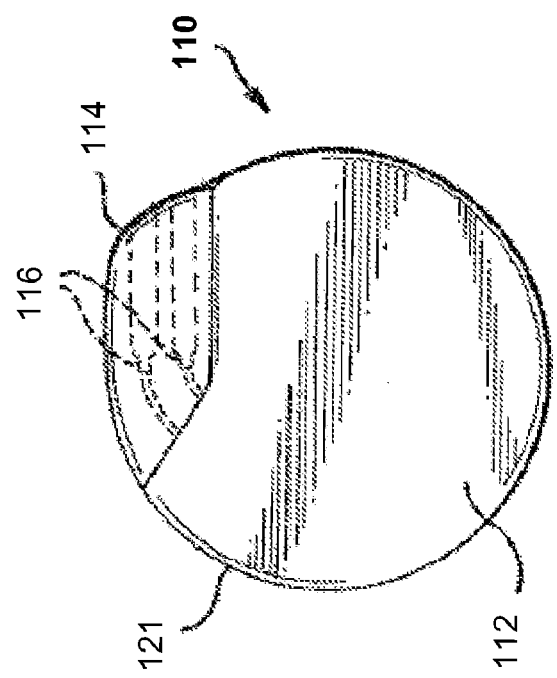
Figure 1B:
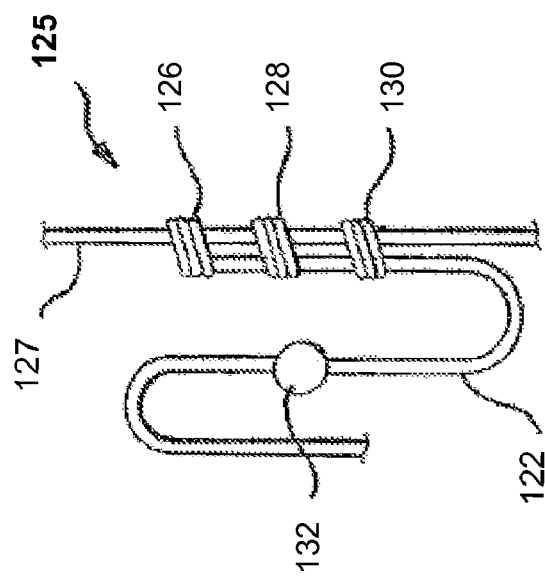

Turning now to FIGS. 1A-1C, stylized diagrams are provided of an implantable medical device implanted into a patient's body for providing electrical stimulation to a portion of the patient's body, in accordance with one illustrative embodiment of the present invention. FIGS. 1A-1C depict a stylized implantable medical system 100 for implementing one or more embodiments of the present invention. FIGS. 1A-1C illustrate an electrical signal generator 110 having a main body 112 comprising a case or shell 121 with a header 114 (FIG. 1C) for connecting to at least one lead. The electrical signal generator 110 is implanted in the patient's chest in a pocket or cavity formed by the implanting surgeon just below the skin (indicated by a line 145, FIG. 1A), similar to the implantation procedure for a pacemaker pulse generator.

A stimulating nerve electrode assembly 125 (FIG. 1B) is conductively coupled to the distal end of an insulated, electrically conductive lead assembly 122, which preferably comprises one wire for each electrode 126, 128 of the electrode assembly 125. The lead assembly 122 is conductively coupled at its proximal end to connectors 116 of the header 114 of case 121. The electrode assembly 125 may be surgically coupled to a vagus nerve 127 in the patient's neck (FIGS. 1A, 1B) or at another location, e.g., near the patient's diaphragm (not shown). The electrical signal may also be applied to other cranial nerves, e.g., the trigeminal or glossopharyngeal nerves. The electrodes 126, 128 of the electrode assembly 125 are preferably wrapped around the vagus nerve, and may be secured to the vagus nerve 127 by a spiral anchoring tether 130 (FIG. 1B) such as that disclosed in U.S. Pat. No. 4,979,511, issued Dec. 25, 1990, to Reese S. Terry, Jr., and assigned to the same assignee as the instant application. The lead assembly 122 can be secured, while retaining the ability to flex with movement of the chest and neck, by a suture connection 132 to nearby tissue (FIG. 1B).

In one embodiment, the electrode assembly 125 has an open helical design, which is self-sizing and flexible to minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises at least one ribbon electrode, of a conductive material such as platinum, iridium, platinum-iridium alloys, or oxides of the foregoing.

In one embodiment, the IMD is used to perform active stimulation in response to an input received by the IMD from a sensor. Other embodiments of the present invention use passive stimulation to deliver a continuous, periodic, or intermittent electrical signal to the vagus nerve according to a programmed on/off duty cycle without the use of sensors to trigger therapy delivery. Both passive and active stimulation may be combined or delivered by a single IMD 200 according to the present invention. Either or both modes may be appropriate to treat the particular disorder diagnosed in the case of a specific patient under observation.

The electrical signal generator 110 may be programmed with an external computer 150 using programming software of the type copyrighted by the assignee of the instant application with the Register of Copyrights, Library of Congress, or other suitable software based on the description herein. In one embodiment, a programming wand 155 can be used to facilitate radio frequency (RF) communication between the computer 150 (FIG. 1A) and the pulse generator 110. The programming wand 155 and software permit non-invasive communication with the generator 110 after the latter is implanted. The programming wand 155 is preferably powered by internal batteries and provided with a "power on" light to indicate sufficient power for communication. Another indicator light may be provided to show that data transmission is occurring between the wand and the generator. In an embodiment using RF frequencies in the Medical Implants Communications Service (MICS) bands, the wand 155 may be omitted.

By providing the therapeutic electrical signal, the electrical signal generator 110 may treat a disorder or a medical condition of a patient. A generally suitable form of neurostimulator for use in the method and apparatus of the present invention is disclosed, for example, in U.S. Pat. No. 5,154,172, assigned to the same assignee as the present application. A commercially available example of such a neurostimulator is available from Cyberonics, Inc., Houston, Texas, the assignee of the present application. Certain parameters defining the therapeutic electrical signal generated by the electrical signal generator 110 are programmable, such as by means of an external programmer in a manner conventional for implantable electrical medical devices.

Figure 2:
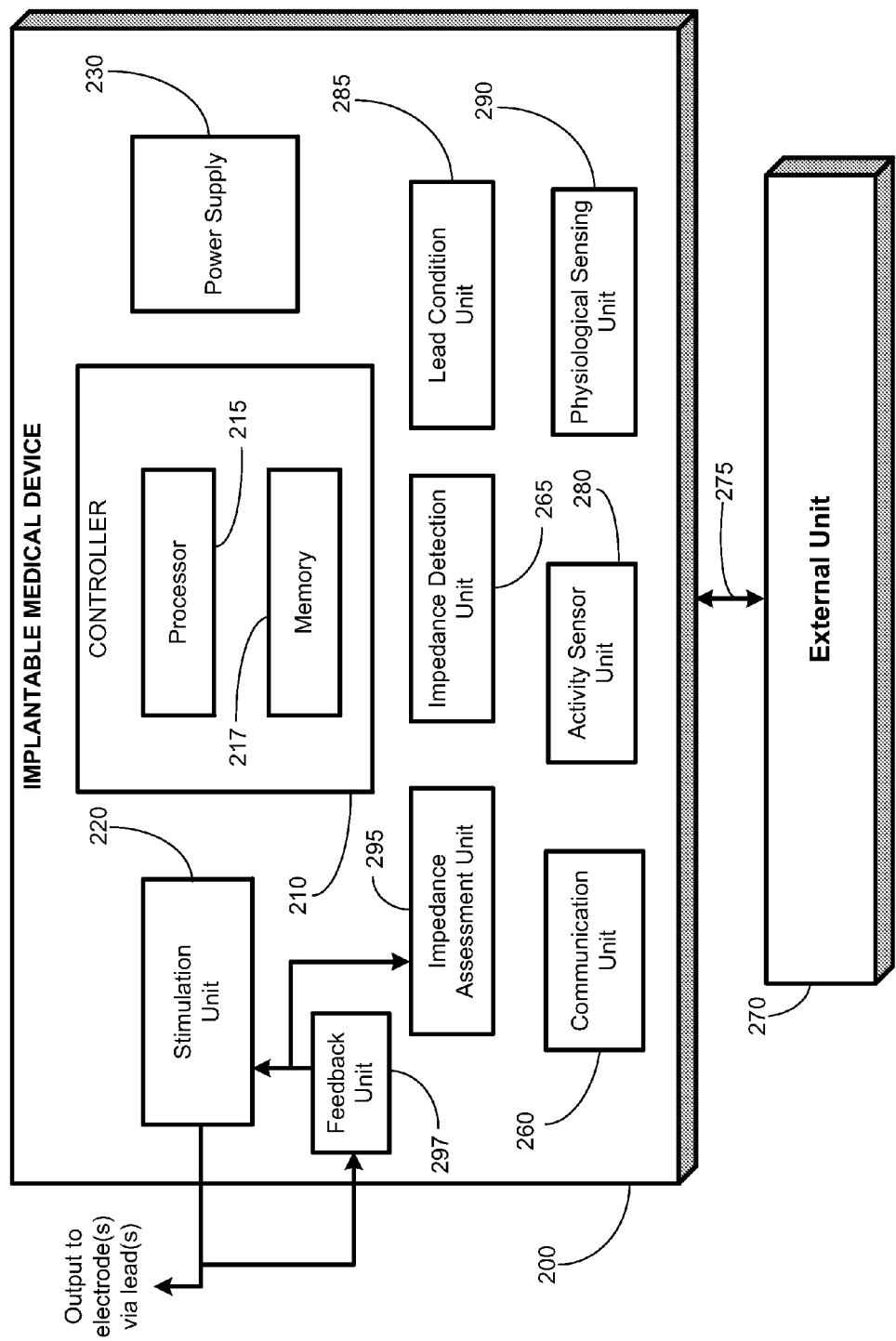
FIG. 2 is a block diagram of an implantable medical device and an external unit that communicates with the implantable medical device, in accordance with one illustrative embodiment of the present invention.

Turning now to FIG. 2, a block diagram depiction of an implantable medical device (IMD), in accordance with one illustrative embodiment of the present invention is illustrated. The IMD 200 may be used for stimulation to treat various disorders, such as epilepsy, depression, bulimia, traumatic brain injury, heart rhythm disorders, etc. The IMD 200 may be coupled to various electrodes associated with the leads (FIG. 1A). Therapeutic electrical signals may be transmitted from the IMD 200 to target areas of the patient's body, specifically to various electrodes associated with the leads. Therapeutic electrical signals from the IMD 200 may be transmitted via the leads to stimulation electrodes associated with the electrode assembly 125 (FIG. 1B). Further, signals from sensor electrodes, e.g., 125 (FIG. 1A) associated with corresponding leads may also traverse the leads back to the IMD 200.

Referring again to FIG. 2, the IMD 200 may comprise a controller 210 capable of controlling various aspects of the operation of the IMD 200. The controller 210 is capable of receiving internal data and/or external data and generating and delivering a stimulation signal to target tissues of the patient's body. For example, the controller 210 may receive manual instructions from an operator externally, or may perform stimulation based on internal calculations and programming. The controller 210 is capable of affecting substantially all functions of the IMD 200. The controller 210 is capable of detecting various lead health parameters and performing a lead health analysis. Further, the controller 210 is capable of performing one or more remedial actions based upon an assessment of the lead health, which is further described herein.

The controller 210 may comprise various components, such as a processor 215, a memory 217, etc. The processor 215 may comprise one or more microcontrollers, microprocessors, etc., that are capable of performing various executions of software components. The memory 217 may comprise various memory portions where a number of types of data (e.g., internal data, external data instructions, software codes, status data, diagnostic data, etc.) may be stored. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering stimulation signals to one or more electrodes via leads. A number of leads 122 may be coupled to the IMD 200. Therapy may be delivered to the leads 122 by the stimulation unit 220 based upon instructions from the controller 210. The stimulation unit 220 may comprise various circuitry, such as stimulation signal generators, impedance control circuitry to control the impedance "seen" by the leads, and other circuitry that receives instructions relating to the type of stimulation to be performed. The stimulation unit 220 is capable of delivering a controlled current stimulation signal to a target tissue over the leads 122 via one or more electrodes 125.

In one embodiment, the stimulation unit 220 receives a feedback signal indicative of the therapeutic electrical signal that was delivered to a target portion of patient's body via the leads and electrodes. The feedback signal may comprise information as to whether portions of the therapeutic signal sent to the leads from the stimulation unit 220 resulted in a lead voltage that was within a predetermined range as compared to a predicted voltage level. The predicted voltage level relates to a maximum acceptable lead impedance and the known controlled current value of the therapeutic electrical signal. Using principles of Ohm's Law, the predicted voltage may be calculated based upon the maximum acceptable impedance and the controlled current value. In one embodiment, the feedback signal may comprise information relating to each pulse of the therapeutic electrical signal delivered by the stimulation unit 220. A more detailed illustration of the stimulation unit 220 is provided in FIG. 3 and accompanying description below.

As shown in FIG. 2, the IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 is a computer system that is capable of executing a data-acquisition program. The external unit 270 may be controlled by a healthcare provider, such as a physician, at a base station, for example, in a doctor's office. The external unit 270 may be a computer, preferably a handheld computer or PDA, but may alternatively comprise any other device that is capable of electronic communications and programming, e.g., a programmable cell phone. The external unit 270 may download various parameters and program software into the IMD 200 for programming the operation of the implantable medical device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

The IMD 200 also comprises a feedback unit 297 that is capable of receiving a signal indicative of at least a portion of the therapeutic electrical signal delivered by the stimulation unit 220 (i.e., at least a portion—e.g., one or more pulses of a pulsed electrical signal—of the output signal that is fed back to the IMD 200). Based upon the signal indicative of the output signal provided by the IMD 200, the feedback unit 297 is capable of determining whether the voltage level of the signal is below or above a predetermined threshold. This threshold may relate to the expected voltage of the lead based upon the expected or maximum desired impedance of the lead and the known current controlled signal provided by the IMD 200. If the voltage of the signal is lower than the predetermined threshold, the feedback unit 297 asserts a feedback signal, $V_{low}$. Assertion of $V_{low}$ by the feedback unit may indicate that the impedance of the lead is higher than expected. Further details relating to the feedback are provided below. This principle may also be applied conversely, wherein if the voltage signal is higher than another predetermined threshold, the feedback unit 297 asserts another feedback signal, $V_{high}$. The assertion of $V_{high}$ may indicate that the lead impedance is too low and that an electric short circuit may exist in the leads.

The IMD 200 may also comprise an impedance detection unit 265. The impedance detection unit 265 is capable of acquiring impedance data relating to leads coupled to the IMD 200. The impedance detection unit 265 is capable of performing measurements at pre-determined intervals, or upon a command from the controller 210.

The IMD 200 may also comprise an impedance assessment unit 295. The impedance assessment unit 295 receives the feedback signal described above. The impedance assessment unit 295 is capable of calculating the impedance of the leads based upon the value of the feedback signal. The impedance assessment unit 295 determines whether a charge device (e.g., capacitor) voltage that may be used to deliver a therapeutic electrical signal is operating at a sufficient level for a desired output controlled current, based upon known or predetermined impedance value of the leads. Therefore, for a known lead impedance value and a desired controlled current value, using Ohm's Law, the expected voltage across the lead terminal is determined. When the signal that is fed back from the IMD 200 output signal provided by stimulation unit 220 is compared to the expected voltage value, the feedback signal ($V_{low}$) is asserted if the actual voltage is below a tolerance range from the expected voltage value. Similarly, if $V_{high}$ were asserted, the impedance assessment unit 295 may determine that an electrical short has occurred.

The assertion of the feedback signal, $V_{low}$, indicates whether the voltage was excessively low, even though the controlled current therapeutic signal should have resulted in the expected voltage across the lead terminals. If the controlled current therapeutic signal did not result in the expected voltage across the lead terminal based upon predicted maximum lead impedance, a deduction can be made that a change in the actual lead impedance caused the voltage discrepancy. This change in the actual lead impedance may be indicative of a lead condition problem, e.g., a lead break or a short in the conductor(s) associated with the lead. Therefore, under certain circumstances, an assertion of the feedback signal, $V_{low}$, would be indicative of a potential lead problem that may have occurred during a delivery of a particular stimulation signal. Since the feedback signal is indicative of whether a voltage resulting from the delivered control current was improperly low or not, the assertion of $V_{low}$ can be recorded to determine particular moments of lead condition problems. By, for example, taking multiple measurements at predetermined time intervals after assertion of $V_{low}$, the impedance assessment unit 295 is able to deduce whether the occurrences of high impedance based upon detection of the $V_{low}$ signal relates to intermittent lead condition problems or to a more permanent lead condition problem.

The IMD 200 also comprises an activity sensor unit 280. The activity sensor unit 280 is capable of detecting one or more activities performed by the patient. The activity sensor unit 280 may be capable of keeping track of a particular activity during delivery of a particular stimulation signal. Therefore, the IMD 200 is capable of correlating instances of high impedance occurrences detected by the impedance assessment unit 295, with data from the activity sensor unit 280. In this manner, correlation of particular activities to potential lead condition problems may be performed. Thus, a correlation of particular activities to potential lead problems may be discovered.

Still further, the IMD 200 may comprise a physiological sensing unit 290. The physiological sensing unit 290 is capable of deciphering a number of physiological parameters relating to the patient. In addition to one or more electrodes attached to the patient's cranial nerve (e.g., vagus nerve), one or more additional electrodes can also be provided and connected to the IMD 200. Such other electrodes can function as sensing electrodes to sense any target parameter in the patient's body. For example, an electrode may be coupled to the patient's heart to sense the electrical activity of the heart. Sensing electrodes may be additionally or alternatively attached to other tissues of the body in addition to, or instead of, the patient's heart. In some embodiments, sensors besides electrodes can be included to sense various parameters of the patient. The term "sensor" is used herein to encompass both electrodes and other types of sensing elements. Sensors used in conjunction with the IMD 200 may comprise electrodes that sense an electrical signal (e.g., a voltage indicative of neural or brainwave activity), a pressure transducer, an acoustic element, a photonic element (i.e., light emitting or absorbing), a blood pH sensor, a blood pressure sensor, a blood sugar sensor, a body movement sensor (e.g., an accelerometer), a temperature sensor (e.g., a thermocouple) or any other element capable of providing a sensing signal representative of a physiological body parameter. Any one of a variety of suitable techniques can be employed to run a lead from an implantable device through a patient's body to an attachment point, such as the vagus nerve, or cardiac or other tissue. In some embodiments, the outer surface of the IMD 200 itself may be electrically conductive and function as a sensor as well. The IMD 200 is capable of correlating particular physiological parameters to episodes of high impedance, i.e., lead condition problems. Therefore, the IMD 200 is capable of detecting lead condition errors and correlating them to a particular time period, particular activity and/or particular physiological parameters.

The IMD 200 may also comprise a lead condition detection unit 285. The lead condition detection unit 285 is capable of assessing the health or condition of the lead(s) coupled to the IMD 200 based upon various parameters, e.g., data from the impedance detection unit 265 and/or the impedance assessment unit 295. Based upon the condition of the lead, a determination is made as to whether the lead problem is a constant/permanent problem, or an intermittent problem. The lead condition detection unit 285, in one embodiment, is capable of determining the severity and the type of intermittent or permanent lead problem that may be detected. Further, in one embodiment, the lead condition detection unit 285 may perform a ranking type function, ranking the degree of the severity of the lead health (e.g., ranking an error as a rare, serious intermittent error, a frequent, minor intermittent error, or a constant, major error). Using data from the impedance assessment unit 295, the lead condition unit 285 may verify lead condition problems found by the impedance detection unit 265, and/or vice versa. Often, intermittent errors not discovered by the impedance detection unit 265 may be found by the impedance assessment unit 295. Further, in order to conserve power, the IMD 200 may limit usage of the impedance detection unit 265 and rely more heavily upon impedance assessment unit 295, since the implementation of the unit 295 is based upon generally existing feedback signal, resulting in less overhead.

In instances where an intermittent lead condition problem is detected, the IMD 200 may enter an alternative/secondary operation mode (as opposed to a normal operation mode when no lead condition problems are detected). The alternative/secondary operation mode of the IMD 200 may take on various forms of modified delivery of stimulation signals, such as a reduction in the energy output provided by the stimulation electrical signal. This may take the form of a therapeutic electrical signal in which a parameter defining the signal is reduced to a value less than in a normal operation mode. Thus, a therapeutic electrical signal in an alternative/secondary mode operation may have a reduced current, pulse width, frequency, on-time, or an extended off-time, as compared to the therapeutic electrical signal provided during normal operation mode.

Other implementations of a secondary operation, such as a pre-stimulation operation check mode may also be implemented. The pre-stimulation operation mode may include performing an assessment of the lead health immediately prior to delivery of a therapeutic electrical signal burst. The pre-stimulation assessment may include a pre-determined set of diagnostic-type tests that may be performed substantially immediately before the delivery of a therapeutic electrical signal burst. Other operational modifications, such as turning off a particular lead, may also be performed. In this manner, a different type of stimulation that includes a different set of electrode usage for delivery of therapy may be provided during operation in the alternative/secondary operation mode. Further, other reactions, such as utilizing a uni-polar delivery of stimulation therapeutic signal may be implemented. The uni-polar mode may include delivery of a stimulation signal via a single lead, wherein the electrical reference points (anode and cathode) are a lead tip (such as a lead tip electrode not experiencing a lead problem) and the chassis (or can) of the IMD 200.

It will be recognized that one or more of the blocks 210-290 (which may also be referred to as modules) may comprise hardware, firmware, software, or any combination thereof Additionally, one or more blocks illustrated in FIG. 2 may be combined with other blocks, which may represent circuit hardware units, software algorithms, etc. Some of these modules may reside or may be merged into the controller 210. Additionally, any number of the circuitry or software units associated with the various blocks illustrated in FIG. 2 may be combined into a programmable device, such as a field programmable gate array, an ASIC device, etc.

Figure 3:
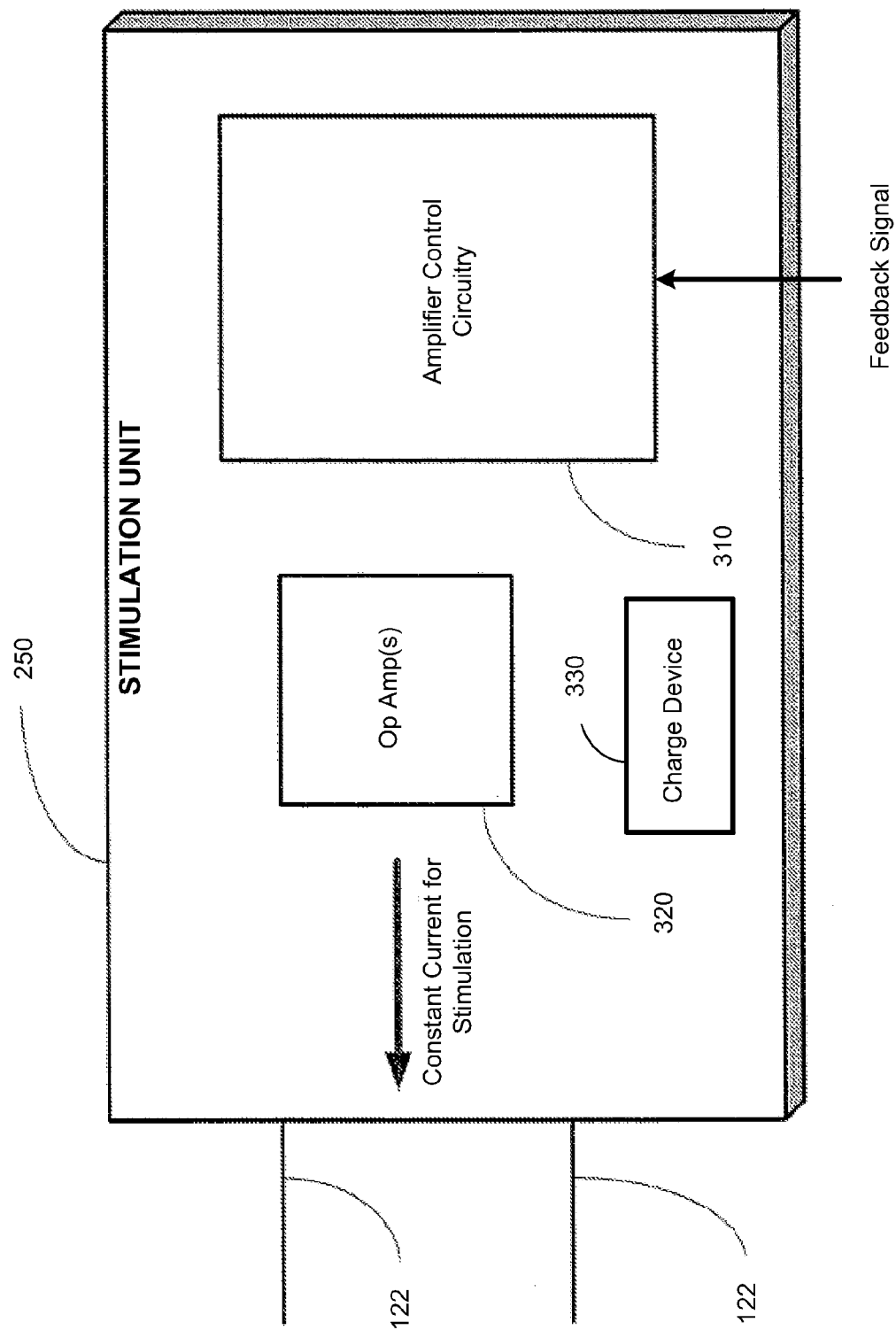
FIG. 3 provides a more detailed block diagram depiction of a stimulation unit of FIG. 2, in accordance with one illustrative embodiment of the present invention.

Turning now to FIG. 3, further details of a block-diagram depiction of one embodiment of the stimulation unit 220 of FIG. 2, are provided. The stimulation unit 220 of the IMD 200 comprises an op amp unit 320, which may comprise one or more operational amplifiers that are capable of delivering a controlled therapeutic electrical current signal for stimulation. In one embodiment, the controlled current is a constant current or a substantially constant current. The stimulation unit 220 may also comprise an amplifier control circuitry unit 310 that may contain circuitry and/or programmable logic to control the operation of the op amps 320. The simulation unit 220 also comprises a charge device 330. The charge device 330 may be a capacitor, an inductor, or any device capable of storing and discharging electrical charge. Additionally, the stimulation unit 220 may be coupled to leads 122, which may comprise a pair of signal wires capable of delivering an electrical signal to an electrode pair 125-1 and 125-2 (FIG. 1B) each coupled to a distal end of one of the leads. The leads 122 (and the electrodes 125-1 and 125-2) are capable of providing a complete circuit between the IMD 200 and the region of the body/tissue to which the electrodes are attached, which may be approximated as an equivalent impedance. Each lead 122 may comprise a single strand wire or, more preferably, a multi-strand wire braided or otherwise coupled together as a single functional wire. Each of the two lead wires in this embodiment is provided with a separate socket and connector 116, as shown in FIG. 1C. In another embodiment, two leads may be combined into a single coaxial cable (as shown in FIGS. 1A and 1B), with a single socket providing both coaxial connectors 116.

Embodiments of the present invention provide for utilizing the delivery of a constant current signal for providing a therapeutic electrical signal, and measurement of the impedance experienced by the leads. In a preferred embodiment, the controlled or constant current signal provided by the stimulation unit 220 is independent of the impedance experienced across the leads 122. For example, even if the impedance experienced across the leads changes, the op amp 320, in conjunction with the amplifier control circuitry 310, adjusts to deliver a controlled or constant current despite the change in the impedance experienced across the leads.

Since a controlled, constant current is delivered despite variations in the impedance across the leads, the voltage across the lead terminals may be used to provide an indication of the lead impedance. For example, if the nerve tissue to which the leads are connected has an impedance of 1000 ohms, a particular stimulation may call for a one milliamp constant current signal. In this case, even if a 5000 ohms impedance is experienced across the leads, the stimulation unit 220 will still provide a one milliamp current. Hence, the power may vary but the current remains constant. In other words, the op amp 320 will stabilize itself utilizing various circuitry, including the amplifier control circuitry 310, to provide a constant current signal even if the impedance experienced by the leads varies during the period the signal is provided. Therefore, using Ohm's Law, V=IR, a measurement of the voltage across the leads will provide an indication of the actual impedance experienced by the leads.

In one embodiment, the amplifier control circuitry 310 may receive one or more feedback signals ($V_{low}$ and/or $V_{high}$) that indicate whether an output voltage across the lead was respectively lower or higher than expected. Based upon this feedback, the amplifier control circuitry 310 is capable of controlling the charge device 330 for delivering the signal with appropriate voltage levels. In other words, based upon the feedback signal, the amplifier control circuitry 310 may increase the energy related to the voltage provided by the stimulation unit 220 in order to increase the resultant voltage. The charge device 330 is capable of storing a charge and later delivering that change at desired voltages and currents to provide the therapeutic electrical signal. Therefore, based upon the feedback signal, the amplifier control circuitry 310 is capable of controlling output of the charge device 330. The feedback signal $V_{low}$ is capable of controlling the operation of the stimulation unit 220 such that desired levels of voltage on the leads are provided based upon the controlled current input.

Figure 4:
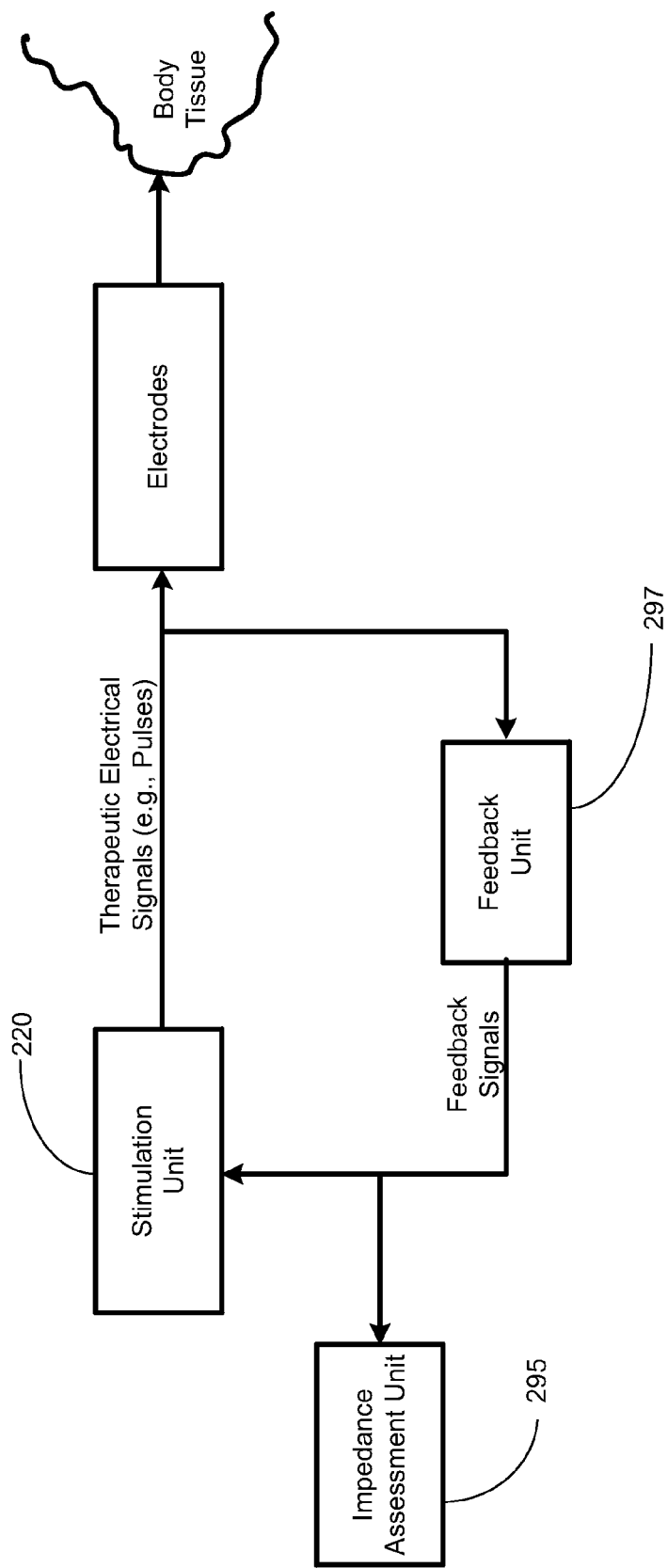
FIG. 4 illustrates a stylized, block diagram depiction of a feedback signal being used to perform an impedance calculation, in accordance with one embodiment of the present invention.

Turning now to FIG. 4, a stylized block diagram depiction of a feedback path associated with the delivery of a therapeutic signal, in accordance with one embodiment of the present invention, is provided. As illustrated in FIG. 4, the stimulation unit 220 provides therapeutic electrical signals that comprise electrical pulses for stimulating a target body tissue of the patient. The electrical pulses that, in some embodiments, comprise the therapeutic electrical signal are sent via the leads to electrodes that are electrically coupled to the target body tissue. The electrical pulses may also be provided to the feedback unit 297. The feedback unit 297 is capable of comparing the voltage level of a pulse in the therapeutic electrical signal with a predetermined threshold. The predetermined threshold may relate to the expected voltage across the lead based upon the expected impedance of the lead and the known value of the pulse current provided by the stimulation unit 220. Based upon the comparison performed by the feedback unit 297, one or more feedback signals are either asserted or not asserted. If the voltage of the pulse signal is detected to be lower than the predetermined threshold, the feedback signal, $V_{low}$ is asserted and sent to the stimulation unit 220. If the voltage of the pulse signal is detected to be higher than the predetermined threshold, the feedback signal, $V_{high}$, is asserted and sent to the stimulation unit 220. The stimulation unit 220 may then adjust the current or voltage value of the pulse signal to compensate for $V_{low}$ or $V_{high}$ being asserted. If either $V_{low}$ or $V_{high}$ is not asserted, the stimulation signal continues with the present value of the controlled current signal.

The impedance calculation unit 295 also receives the feedback signals along with the stimulation unit 220. As described above, the impedance calculation unit 295, upon detection of $V_{low}$ or $V_{high}$ being asserted, determines whether the voltage associated with the charge device 330 is at a sufficient level to provide a therapeutic electrical signal have a desired current for a predetermined maximum impedance. The assertion of either of $V_{low}$ or $V_{high}$ during the delivery of the therapeutic electrical signal may be indicative of a lead condition problem. A single instance or sporadic assertion of $V_{low}$ or $V_{high}$ may provide an indication of an intermittent lead condition problem, while a repeated assertion of the signals may indicate the emergence of a sudden but persistent or permanent lead condition problem. Occurrences of these lead condition problems may be stored, reported, correlated, and/or otherwise processed for analysis of the type of intermittent problems experienced by the lead.

Figure 5:
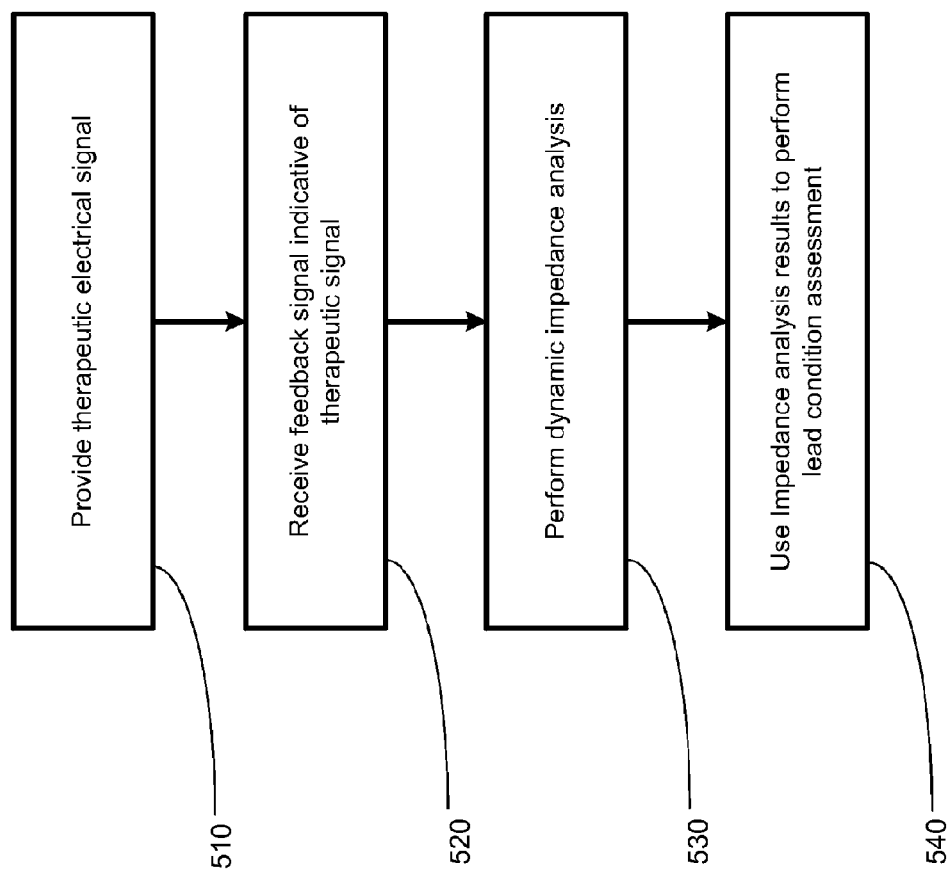
FIG. 5 illustrates a flowchart depiction of performing a dynamic lead condition assessment, in accordance with one embodiment of the present invention.

Turning now to FIG. 5, a flowchart depiction of a method for performing an assessment of lead condition problems, in accordance with one illustrative embodiment of the present invention, is provided. The IMD 200 may provide a therapeutic electrical signal for providing a therapeutic electrical signal to a target portion of a patient's body (block 510). The therapeutic electrical signal is a controlled current signal, wherein its current is known and controlled by the IMD 200. Upon providing the therapeutic electrical signal, the IMD 200 may receive a feedback signal that is indicative of the voltage for at least a portion of the therapeutic electrical signal (block 520). This step may include comparing the received signal indicative of the voltage of a pulse in a pulsed therapeutic electrical signal with a threshold voltage and determining whether the feedback voltage signal is above or below the predetermined threshold. The threshold voltage may relate to an expected voltage level based upon an expected or maximum impedance of the lead, and the known current of the current controlled stimulation signal. In one embodiment, receiving the feedback signal may comprise receiving a multiplicity of feedback signals indicative of the voltage in a corresponding multiplicity of pulses in a pulsed therapeutic electrical signal. This step may also include asserting the $V_{low}$ or $V_{high}$ feedback signals for each pulse in which the feedback voltage is lower or higher than the threshold voltage(s).

Based upon the feedback signal(s), the IMD 200 may then perform a dynamic impedance process analysis (block 530). The dynamic impedance process analysis includes performing a dynamic analysis of the lead condition. In other words, based upon the feedback signal(s) (i.e., $V_{low}$ and/or $V_{high}$) the IMD 200 is capable of determining whether a lead condition problem exists during a time period when the therapeutic signal is delivered. This assessment may be made in a variety of time frames, from periodic assessment to an assessment made on each pulse delivered by the IMD 200 for stimulation therapy. Where a multiplicity of feedback signals are received in step 520, the dynamic impedance analysis of block 530 allows a continuous or nearly continuous evaluation of the status of the lead. In one embodiment, a continuous data stream is developed to indication each pulse in the therapeutic signal for which a lead condition problem exists, as indicated by the assertion of $V_{low}$ and/or $V_{high}$. In each instance of excessively low or high voltage, the time at which the pulse occurred, and the actual voltage value measured, may be recorded and stored. In other words, the dynamic impedance analysis allows for an ongoing, continuous or near-continuous assessment of whether an intermittent or permanent lead condition problem exists. A more detailed description of the dynamic impedance analysis is provided by FIG. 6 and accompanying description below.

Upon performing the dynamic impedance analysis, the IMD 200 is capable of using the impedances to perform a continuous or near-continuous lead condition assessment (block 540). The lead condition assessment may be made by, e.g., the impedance assessment unit 295, the impedance detection unit 265, and/or the lead condition unit 285 to provide a historical record of lead condition/health of the leads 122 for the IMD 200 over time. Further, qualitative information may also be provided concerning the nature and/or magnitude of the lead condition problem. The continuous or nearly-continuous assessment of the lead condition may allow, for example, early detection of an intermittent break in a few strands of a multi-strand lead wire, as indicated by initially temporary, small variations from a previously constant or nearly constant feedback voltage. The lead condition assessment may include determining periods of time when a lead condition problem was detected. This data may be correlated to various time periods, physical activity, physiological parameters, etc. More detailed illustrations of the step of performing the lead condition assessment of block 540 is provided in FIGS. 7 and 8, and accompanying description below.

Figure 6:
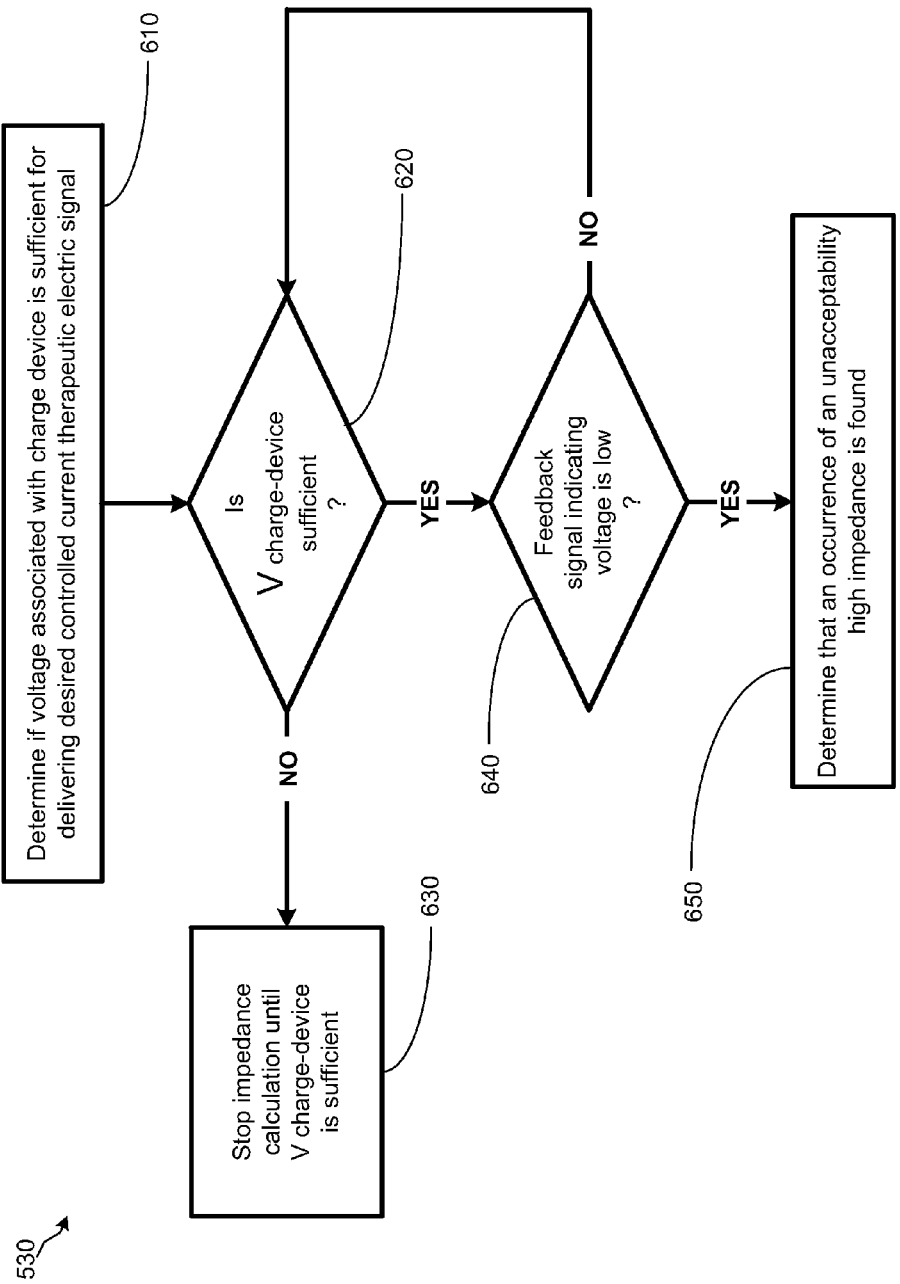
FIG. 6 illustrates a flowchart depiction of performing the step of performing a dynamic lead impedance analysis of FIG. 5, in accordance with one embodiment of the present invention.

Turning now to FIG. 6, a flowchart providing additional details for one embodiment of the step of performing a dynamic impedance analysis (step 530) in FIG. 5. Upon receiving a feedback signal indicative of the voltage level (step 520), in one embodiment a determination is made whether the voltage associated with the charge device 330 is sufficient for delivering a desired controlled current pulse in the therapeutic electrical signal in light of the maximum desired lead impedance (block 610). The IMD 200 determines whether the voltage associated with the charge device ("$V_{charge-device}$") is sufficient to ensure that an acceptable desired lead impedance for the desired current output is achieved (block 620). In other words, a determination is made whether the $V_{charge-device}$ is at a sufficient level based upon the following application of the principle of Ohm's Law, as defined by Equation 1.

$$V_{charge-device}/\text{output current} >= (\text{the lead impedance}) \quad \text{Equation 1}$$

If a determination is made that the voltage of the charge device 330 ($V_{charge-device}$) is not sufficient, the impedance calculation may be suspended until the $V_{charge-device}$ is deemed sufficient (block 630). Upon a determination that $V_{charge-device}$ is sufficient to provide the pulse as programmed for the therapeutic electrical signal, as described above, a determination is made as to whether the feedback signal(s) indicating whether the voltage is below a first threshold or above a second threshold (i.e., $V_{low}$ and $V_{high}$) have been asserted (block 640). If either $V_{low}$ or $V_{high}$ has not been asserted, the IMD 200 continues normal operations and monitors the $V_{charge-device}$. However, if either $V_{low}$ or $V_{high}$ has indeed been asserted, a determination is made that an occurrence of unacceptably high impedance (i.e., $V_{low}$ was asserted), or unacceptably low impedance (i.e., $V_{high}$ was asserted), has been found (block 650). This occurrence is then recorded and processed, as described below. As previously noted, in some embodiments of the present invention, a multiplicity of feedback signals are received, in which case the foregoing operations are repeated for each feedback signal (i.e., each pulse of the therapeutic electrical signal). This continuous process allows a series of ongoing determinations as to whether or not that the voltage in the charge device 330 is sufficient to continue delivery of the therapeutic electrical signal.

Figure 7:
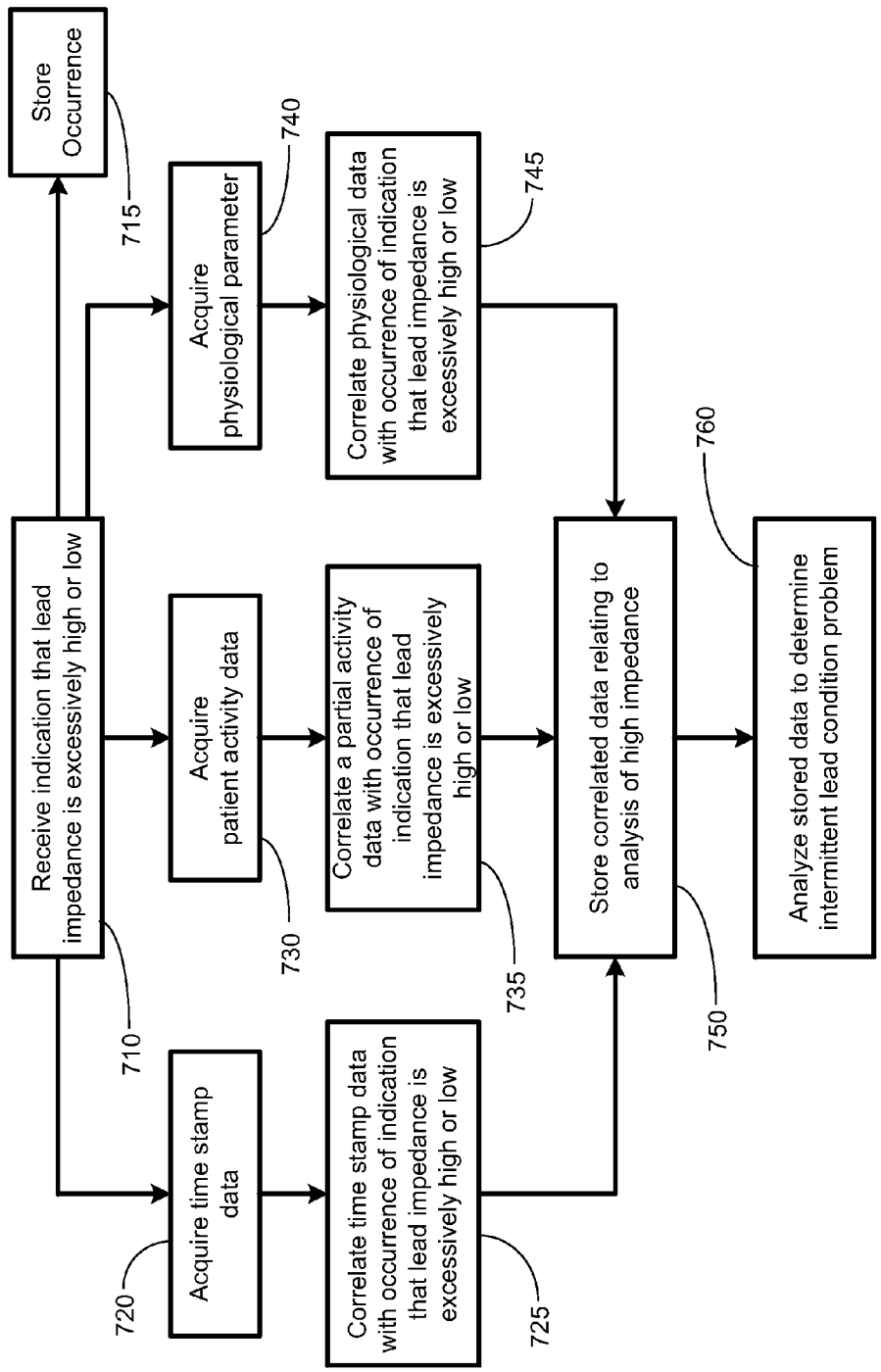
FIG. 7 provides a first illustration of a flowchart depiction of a method of performing a lead condition assessment of FIG. 5, in accordance with a first embodiment of the present invention.

Turning now to FIG. 7, a first embodiment of the step of performing a lead condition assessment described in block 540 of FIG. 5, in accordance with a first embodiment of the present invention, is provided. Upon performing the dynamic impedance analysis (block 530 and FIG. 6), the IMD 200 may receive an indication that the lead impedance is excessively high (block 710). In other words, upon a determination that $V_{charge-device}$ is sufficient and either $V_{low}$ or $V_{high}$ has been asserted, an indication that the lead impedance is either excessively high or excessively low is received. Based upon the detection that the lead impedance is either excessively high or excessively low, in one embodiment, this indication is stored (block 715). The excessively high lead impedance occurrence may be indicative of a lead break, and the excessively low lead impedance occurrence may be indicative of an electrical short in the conductor(s) associated with the lead.

In addition to storing the occurrence of the high or low impedance detection, the IMD 200 may acquire time stamp data relating to the time period of the occurrence (block 720). Based upon the time stamp data, the IMD 200 may correlate the time stamp data with the occurrence of the indication that the lead impedance was excessively high or excessively low (block 725). This correlated time stamped occurrence data may then be stored (block 750).

Similarly, upon receiving the indication that the lead impedance is excessively high or excessively low, the IMD 200 may acquire patient activity data (block 730). In an alternative embodiment, the patient activity data may have been independently acquired in a previous time period. The patient activity data may include data relating to particular activity performed by the patient proximate to the time period when the lead impedance was detected. The IMD 200 may then correlate the patient activity data with the occurrence of indication that the lead impedance was excessively high or low (block 735). This correlated data is then also stored by the IMD 200 (block 750). Still further, upon receiving an indication that the lead impedance is excessively high or excessively low, the IMD 200 may also acquire physiological parameter data (block 740). The IMD 200 may then correlate the physiological parameter data with the indication that the lead impedance was excessively high (block 745). This correlated data is also stored by the IMD 200 (block 750). The IMD 200 may then analyze the stored data to determine whether lead condition problem exists and if so, whether it is intermittent or continuous, serious or not serious (block 760). The correlated data may be analyzed to further quantify the type of intermittent lead condition problems detected, e.g., lead breaks due to certain movements, lead conditions due to certain physiological states, etc.

Figure 8:
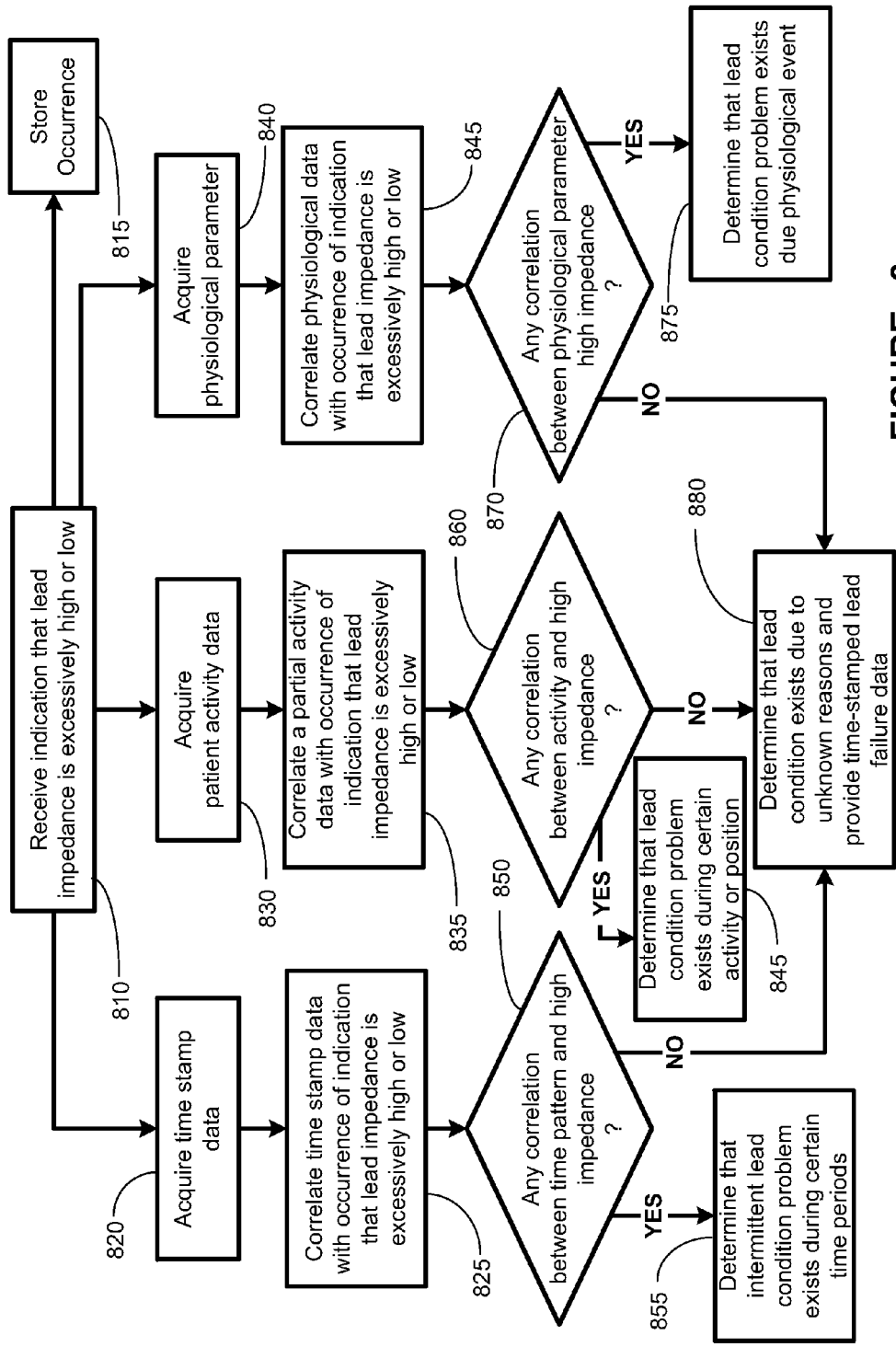
FIG. 8 provides a second illustration of a flowchart depiction of the method of performing a lead condition assessment of FIG. 5, in accordance with a second embodiment of the present invention.

Turning now to FIG. 8, a second flowchart depiction of performing the lead condition assessment of block 540 of FIG. 5, in accordance with a second embodiment of the present invention, is provided. Similar to the description above relating to FIG. 7, FIG. 8 also describes receiving an indication that the lead impedance is excessively high or excessively low and acquiring time stamped data, patient activity data, and physiological data to perform correlation of these activities with excessively high or low impedance (blocks 810-845). Upon correlating the time stamp data with the indication of the lead impedance data (block 825), the IMD 200 may determine whether any correlation exists between any timing pattern (e.g., particular time periods, such as late night-time) to excessively high or low impedance (block 850). If such a correlation is indeed present, the IMD 200 determines that intermittent lead condition problems exist during those time periods (block 855). This information may be used by the healthcare professionals to adjust the lead or modify the patient's routines, etc., to avoid intermittent lead problems.

Further, upon a correlation of patient activity with an occurrence of an indication that the lead impedance is excessively high or excessively low (block 835); a determination is made as to whether there indeed is any correlation between a particular patient activity and excessively high or low impedance (block 860). If there is such a correlation, a determination is made that the lead problem occurs during a particular activity or a physical position of the patient (block 865). This information may be used by a healthcare professional to determine which positions cause the intermittent error and take remedial action. This remedial action may include steps such as taking an x-ray of the patient in such a physical position to determine the location of the lead problem and correcting the lead position. As a further example, a healthcare professional may have the patient move through a series of movements, and using an external device 270 (e.g., a programmable wand), the healthcare professional may be able to pinpoint the exact movements or body position that causes an intermittent lead condition problem.

Further, upon correlating physiological parameter data with an indication that the lead impedance is excessively high (block 845), a determination is made whether any correlation between a physiological condition and the excessively high or excessively low impedance of the lead is present (block 870). Based upon such a correlation, a determination is made that the lead problem occurs during the existence of a particular physiological event, such as increased breathing, increased heart rate, etc. (block 875). This data may be used by a healthcare professional to modify a patient's behavior and/or adjust the lead to avoid or minimize lead condition problems. Based upon a determination that the correlations described above (blocks 850, 860, 870) do not exist, the IMD 200 may determine that the lead condition merely exists due to unknown reasons and may provide a time stamped lead failure data for manual analysis by a healthcare professional (block 880). In this manner, correlation of intermittent lead problems may be made to various activities or time periods, and thus, corrective actions may then be performed. Utilizing embodiments of the present invention, intermittent lead problems that otherwise may have not been detected, may be detected, correlated, analyzed and corrected.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown, other than as described in the claims below. The particular embodiments disclosed above may be altered or modified and all such variations are considered within the scope and spirit of the invention. Accordingly, the protection sought herein is as set forth in the claims below.

What is claimed is:

1. A method comprising:
   providing a therapeutic electrical signal to a lead assembly of an implantable medical device;
   receiving return signals in response to the therapeutic electrical signal, each return signal comprising a voltage signal associated with the lead assembly for a pulse of the therapeutic electrical signal;
   determining, based on the return signals, whether a voltage level of a charge device of the implantable medical device is sufficient to generate a controlled-current level of the therapeutic electrical signal;
   comparing the return signals to a threshold range;
   asserting a feedback signal for each return signal outside the threshold range; and
   determining that a lead condition problem exists when the feedback signal is asserted and the voltage level of the charge device is sufficient to generate the controlled-current level of the therapeutic electrical signal.

2. The method of claim 1, wherein the feedback signal includes a voltage low signal when the return signal associated with a particular pulse is below the threshold range and wherein the feedback signal includes a voltage high signal when the return signal for the particular pulse is above the threshold range.

3. The method of claim 1, further comprising determining that the lead condition problem indicates a lead break when the feedback signal indicates an impedance associated with the lead assembly is above a threshold.

4. The method of claim 1, further comprising determining that the lead condition problem indicates a lead short when the feedback signal indicates an impedance associated with the lead assembly is below a threshold.

5. The method of claim 1, wherein the threshold range comprises a first range above a predicted lead voltage and a second range below the predicted lead voltage, wherein the predicted lead voltage is based on a desired lead impedance and the controlled-current level of the therapeutic electrical signal.

6. The method of claim 1, further comprising performing assessments of lead health prior to delivery of subsequent therapeutic electrical signals after determining that the lead condition problem exists.

7. The method of claim 1, further comprising storing data related to the feedback signal, wherein the data includes a time stamp associated with the feedback signal.

8. The method of claim 1, further comprising acquiring patient activity data; and in response to the feedback signal being asserted at a particular time, storing data related to the feedback signal and the patient activity data associated with the particular time.

9. The method of claim 8, further comprising comparing the patient activity data and the data related to the feedback signal at the particular time with corresponding patient activity data and feedback signal data associated with a second particular time when the feedback signal was asserted; and identifying one or more activities common to the particular time and the second particular time.

10. A method comprising:
    providing a pulsed therapeutic electrical signal to a lead assembly of an implantable medical device;
    measuring a voltage across leads of the lead assembly responsive to each pulse of the pulsed therapeutic electrical signal;
    determining, based on the voltage across the leads of the lead assembly responsive to a particular pulse, whether a voltage level of a charge device of the implantable medical device is sufficient to generate a controlled-current level of the pulsed therapeutic electrical signal;
    asserting a feedback signal when the voltage corresponding to the particular pulse of the pulsed therapeutic electrical signal is outside a threshold range; and
    determining that a lead condition problem exists when the feedback signal is asserted and the voltage level of the charge device is sufficient to generate the controlled-current level of the pulsed therapeutic electrical signal.

11. The method of claim 10, further comprising storing data associated with the feedback signal.

12. The method of claim 10, further comprising determining that the lead condition problem indicates a lead short when the feedback signal indicates an impedance above a threshold.

13. The method of claim 10, wherein the threshold range comprises a first range above a predicted lead voltage and a second range below the predicted lead voltage, wherein the predicted lead voltage is based on a desired lead impedance and the controlled-current level of the pulsed therapeutic electrical signal.

14. The method of claim 10, wherein the feedback signal is a voltage low signal when the voltage corresponding to the particular pulse is below the threshold range and wherein the feedback signal is a voltage high signal when the voltage corresponding to the particular pulse is above the threshold range.

15. The method of claim 10, further comprising acquiring physiological data; and in response to the feedback signal being asserted at a particular time, storing data related to the feedback signal and the physiological data associated with the particular time.

16. The method of claim 15, further comprising comparing the data related to the feedback signal and the physiological data at the particular time with corresponding physiological data and feedback data associated with a second particular time when the feedback signal was asserted; and identifying one or more physiological conditions common between the particular time and the second particular time.

17. A non-transitory computer-readable medium comprising instructions executable by a processor to:
    cause a pulsed therapeutic electrical signal to be applied to a lead assembly of an implantable medical device;
    determine, based on a measured voltage across leads of the lead assembly responsive to a particular pulse of the pulsed therapeutic electrical signal, whether a voltage level of a charge device of the implantable medical device is sufficient to generate a controlled-current level of the pulsed therapeutic electrical signal;
    assert a feedback signal when the measured voltage corresponding to the particular pulse of the pulsed therapeutic electrical signal is outside a threshold range; and
    determine that a lead condition problem exists when the feedback signal is asserted and the voltage level of the charge device is sufficient to generate the controlled-current level of the pulsed therapeutic electrical signal.

18. The non-transitory computer-readable medium of claim 17, wherein the feedback signal is a voltage low signal when the measured voltage corresponding to the particular pulse is below the threshold range and wherein the feedback signal is a voltage high signal when the measured voltage corresponding to the particular pulse is above the threshold range.

19. The non-transitory computer-readable medium of claim 17, wherein the threshold range comprises a first range above a predicted lead voltage and a second range below the predicted lead voltage, wherein the predicted lead voltage is based on a desired lead impedance and the controlled-current level of the pulsed therapeutic electrical signal.

20. The non-transitory computer-readable medium of claim 17, further comprising instructions executable by the processor to determine that the lead condition problem indicates a lead break when the feedback signal indicates an impedance associated with the lead assembly is above a threshold.

21. The non-transitory computer-readable medium of claim 17, further comprising instructions executable by the processor to determine that the lead condition problem indicates a lead short when the feedback signal indicates an impedance associated with lead assembly is below a threshold.

* * * * *